United States Patent [19]

Dreier et al.

[11] Patent Number: 4,722,339

[45] Date of Patent: Feb. 2, 1988

[54] SURGICAL INSTRUMENT

[75] Inventors: Ernst Dreier, Steckborn, Switzerland; Johann Lahodny, Gmünd, Austria

[73] Assignee: Fritz Gegauf ag Bernina - Nahmaschinenfabrik, Steckborn, Switzerland

[21] Appl. No.: 893,773

[22] Filed: Aug. 6, 1986

[30] Foreign Application Priority Data

Sep. 18, 1985 [CH] Switzerland ............... 04045/85-5

[51] Int. Cl.⁴ .................. A61B 17/00; A61B 17/28
[52] U.S. Cl. .............................. 128/321; 128/322; 81/319
[58] Field of Search .............. 128/17, 303 R, 318, 128/321, 322, 326, 340, 346, 354, 323, 324; 81/318–332; 24/517, 640

[56] References Cited

U.S. PATENT DOCUMENTS

| 621,565 | 3/1899 | Harris | 128/340 |
| 1,106,518 | 8/1914 | Matti | 81/319 |
| 3,038,467 | 6/1962 | Sovatkin | 128/17 |
| 3,176,689 | 4/1965 | Yahr | 128/321 |
| 3,470,872 | 10/1969 | Grieshaber | 128/321 |

Primary Examiner—Dalton L. Truluck
Assistant Examiner—F. Wilkens
Attorney, Agent, or Firm—Marks Murase & White

[57] ABSTRACT

The instrument has projections with locking teeth for locking the instrument in its closed clamping position, said projections being located near the connecting zone between the levers of the instrument and their ring grips. Near one projection a slide having a wedge surface is provided, which may be shifted between the projections against spring force by pressure onto a key of the slide, for spreading apart the projections and for disengaging their locking teeth. Disengagement of the locking teeth and opening of the closed instrument are substantially facilitated by simple and inexpensive means which do not hinder operation of the instrument.

10 Claims, 4 Drawing Figures

SURGICAL INSTRUMENT

BACKGROUND OF THE INVENTION

1. Field of the Invention

This invention relates to a surgical instrument having pivotably interconnected levers which may be locked in their closed position by locking means, and disengaging means for releasing the locking means. Prior instruments of this kind such as tongues, hysterectomiums and the like are complicated, expensive, bulky, impractical in operation and tend to hinder and obstruct the operator.

2. Related Art

In an instrument disclosed in U.S. Pat. No. 3,393,680, a pair of levers are equipped with flat actuating plates instead of the usual ring grips, such plates being inclined relatively to the moving plane of the levers. By means of specific differing pressure by the thumb onto the one of these actuating plates, locking teeth rigidly connected to the levers may be engaged or disengaged. Besides the fact that such an instrument may not be used as easily as the instruments with the usual ring grips, it is doubtful whether proper engaging and release of the locking means is achieved.

U.S. Pat. No. 3,038,467 discloses an instrument having a locking mechanism including one part of the locking teeth pivotably mounted on the one of the levers and usually maintained in engaged position by spring force. By pressure with a finger, this part of the locking mechanism may be disengaged against the spring force. This device is bulky and hinders operation of the instrument. Another drawback resides in that the one part of the locking mechanism charged by the full locking forces has to be pivotably connected to one of the levers.

German Pat. No. 20 25 868 discloses an instrument having one of its grips mounted for relative displacement on its lever, and this grip is coupled with a part of a locking device in such a way that this part is brought or held in engagement when the instrument is closed while it is disengaged when the instrument is opened. This mechanism is very complicated, and during the clamping operation the full actuating force acting the grip is transmitted to the disengageable part having the form of a latch of the locking mechanism, whereby high friction and high water occurs.

Due to the foregoing drawbacks, none of the prior solutions has met with success in practice, and instruments which have no auxiliary means for disengaging their locking means are generally used. However, considerable force and skill is required for disengaging the locking means and accurate, sensitive operation of the instrument becomes more difficult.

SUMMARY OF THE INVENTION

This invention aims in providing a simple reliable auxiliary device for disengaging the locking means. The disengaging means comprises a displaceable wedge adapted to be inserted between spreading surfaces in order to force appart and disengage the locking means. In this case, the locking means per se may be of the usual construction and operation, and only a simple additional member is required for disengaging the locking means. The wedge may be part of a slide displaceable against a spring force. This slide may preferably have a pressure key or lug disposed near the connecting portion between one of the levers and its ring grip. This pressure key which is the only slightly projecting and accessible member of the auxiliary equipment is thus located in a protected position between the one lever and its ring grip. Therefore, the key is well protected against involuntary actuation, and on the other hand it is located in a position where it does not hinder the usual operation of the instrument. The key may easily be actuated.

A particularly simple embodiment is obtained if the locking means have lugs or projections rigidly connected to the levers and provided with locking teeth which are engaged or may be engaged automatically by the elasticity of the levers. In this case, the usual construction of the instrument may be maintained and only a very simple additional mechanism is required for spreading the levers against their own elasticity from their locked condition.

The invention will now be described further by way of example with reference to a preferred embodiment illustrated in the accompanying drawings.

DESCRIPTION OF THE PREFERRED EMBODIMENT

Figure 1:
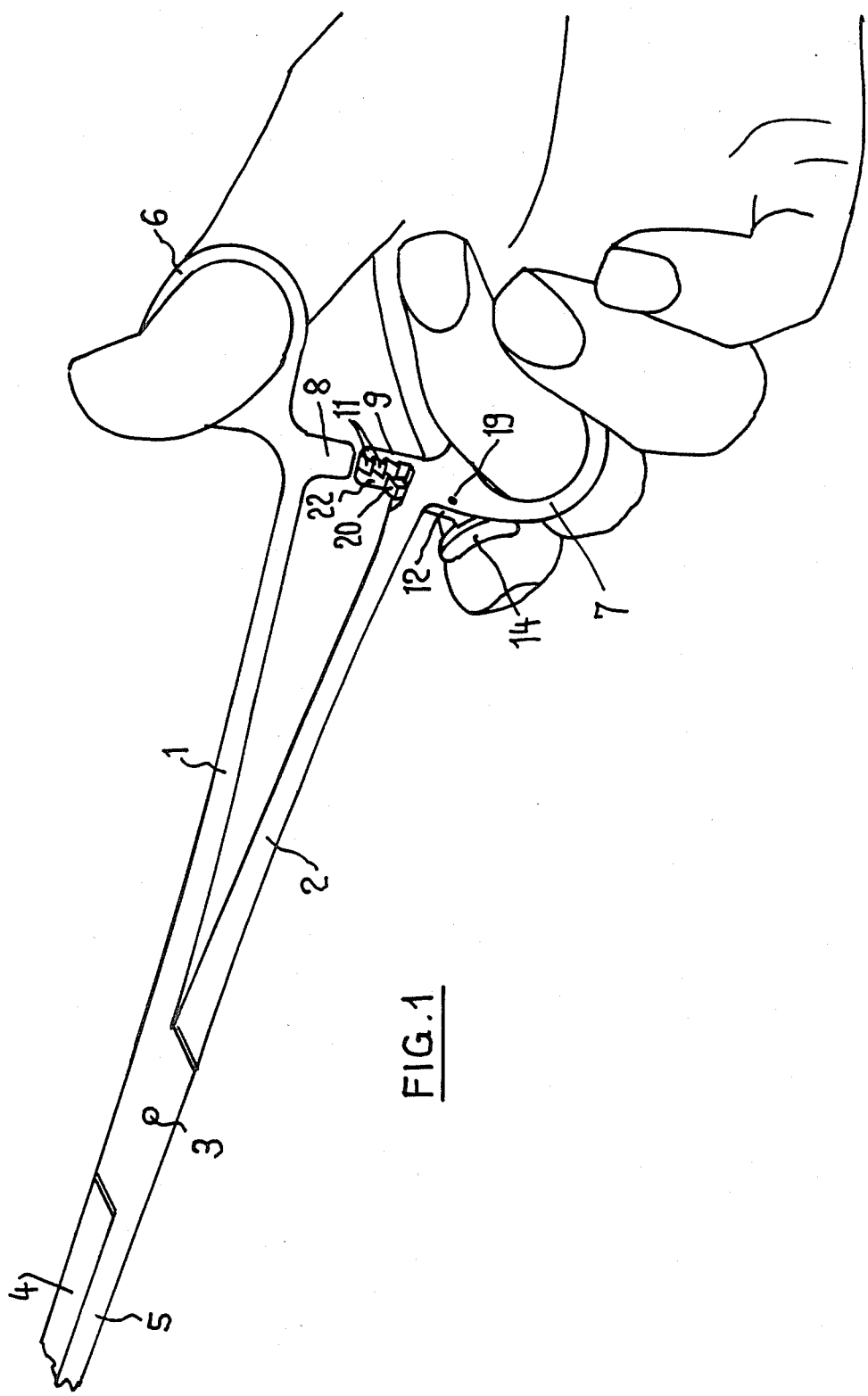
FIG. 1 shows a perspective view of the instrument.
Figure 3:
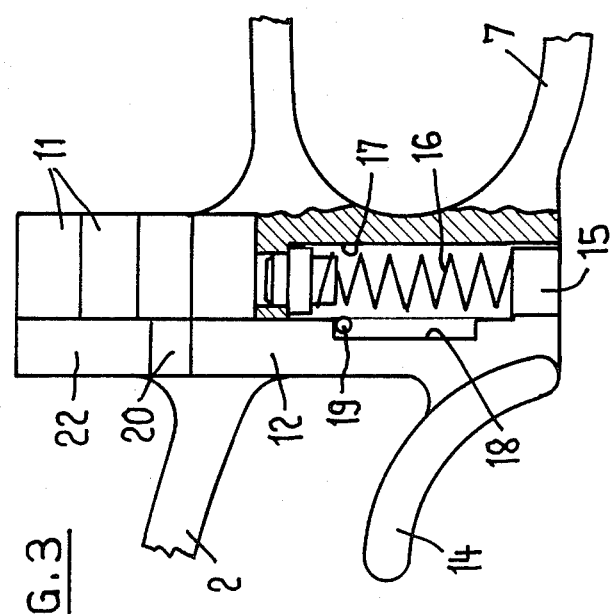
FIGS. 2 and 3 show details of the instrument on a larger scale.

The embodiment illustrated in FIGS. 1 through 4 shows an instrument having two levers 1 and 2 pivotably coupled to each other by means of a shaft 3. The fore ends of the levers 1 and 2 are formed as clamping jaws 4 and 5 of a clamp or tongs.

Ring grips or grip eyes 6 and 7 respectively are formed at the rear ends of levers 1 and 2. Near the connection between each lever 1 and 2 and its ring grip 6 and 7 respectively, are inwardly extending lugs or projections 8 and 9. These projections are formed having each a locking teeth 10 (FIG. 2) and 11 respectively. So far the instrument corresponds to instruments which are actually generally in use. When the tongs or clamp is closed, the locking toothings 10 and 11 laterally engage each other due to the proper elasticity of the levers 1 and 2, and lock the instrument in closed position, that is, if the clamping jaws 4 and 5 sufficiently clamp a tissue not shown in the drawing between them. According to the thickness and kind of the tissue and depending on the pressure exerted the closed position may differ somewhat, this being possibly due to the three-position locking toothing. As mentioned above, it is always difficult to disengage the locked toothings 10 and 11. To this end, it is not only necessary to increase the pressure of the levers 1 and 2 against each other, but these levers must simultaneously be spread laterally from their common plane, that is, a certain distortion of the tongue is required, and this distortion has to be maintained until the instrument is opened sufficiently to prevent reengagement of the locking toothings 10 and 11.

Figure 4:
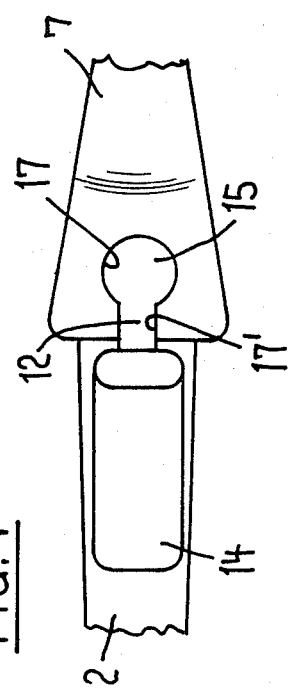
FIG. 4 shows a partial bottom view.
Figure 2:
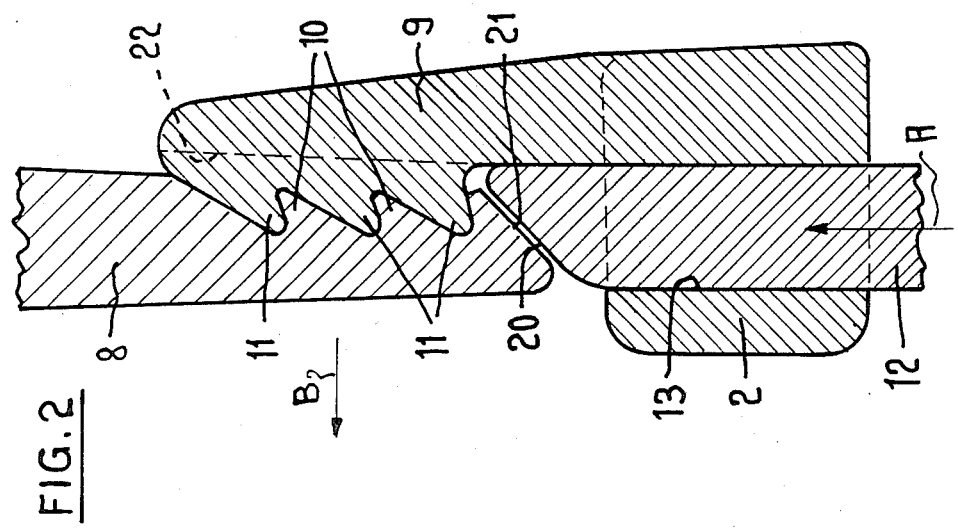

This invention aims in avoiding this drawback by simple, inexpensive auxiliary means requiring little space and forming no obstacle during usual operation of the instrument. To this end an auxiliary device for disengaging the locking toothings is provided near the connection between lever 2 and its ring grip 7. This auxiliary device has a slide 12 the prismatic shaft of which is guided for longitudinal displacement in a guide 13 of the body of the lever 2. A pressure key 14 is formed at the outer end of the slide 12, this key being located in the recess between lever 2 and its ring grip 7, and it is thus well protected against accidental touching and operation. A pressure spring 16 located in a bore 17 of the connection between lever 2 and its ring grip 7 is applied against a projection 15 of the slide 12. By the spring pressure the slide is usually maintained in an outer stop position determined by a stop pin 19 engaging into a longitudinal groove 18 of the slide. As shown in FIG. 4, the slide 12 engages a slit 17' forming an undercut groove together with the bore 17. The projection 15 of the slide 12 has the shape of a circular disc guided with little clearance in the bore 17, thereby forming an additional guide for the slide 12. The inner end of the slide 12 has a wedge surface 20. If the slide 12 is in its inner ineffective position close to the lever 2, it does not hinder full interengagement of the locking toothings into the position shown in FIG. 2. A wedge surface 21 of the projection 8 is located opposite the wedge surface 20 of the slide 12. At the side of the locking toothing 11 of the projection 9 a sliding and supporting surface 22 for the slide 12 is formed. Therefore, the slide 12 may be shifted inwardly from its rest position shown in the drawing, as illustrated by an arrow A in FIG. 2, by pressure onto the key 14, whereby its wedge surface 20 abuts against the wedge surface 21 of projection 8. Thereafter the slide 12 acting as a wedge spreads the projections 8 and 9 (arrow B) and disengages the locking toothings 10 and 11. Thereby the slide 12 is not subject to bending stress because it is always supported on the guiding surface 22 at one side and on the projection 8 at the other side. The projection 8 may also have a guiding and supporting surface for the slide or wedge 12 at the side of the toothing 10.

The operation of the instrument is quite obvious from the foregoing description. As illustrated in FIG. 1, the instrument is seized with the thumb and the middle finger of one hand in order to close the tongs, that is to press the clamping jaws towards each other for clamping a tissue. Thereby the locking toothings 10 and 11 are automatically engaged by the elasticity of the levers 1 and 2. For disengaging the locking device of the closed tongs or clamp, the slide 12 is pressed inwardly by pressure onto the key 14 by the index finger, whereby the slide 12 or its wedge portion respectively is wedged between the projections 8 and 9 for disengaging the locking toothings 10 and 11 against the elasticity of levers 1 and 2. The tongs may then easily be opened by means of the thumb and middle finger. If the key 14 is now released the wedge or slide 12 is returned into its rest position by pressure spring 16, and the instrument is ready for another operation as described above, whereby the locking means are again effective since the slide 12 is in its ineffective rest position.

We claim:
1. A surgical instrument comprising:
   a pair of pivotably interconnected levers having means for engaging an object;
   locking means operatively connected to said pair of levers for maintaining said pair of levers in an engaged position, said locking means having thereon displaceable spreading surfaces; and
   means for disengaging said locking means comprising a displaceable wedge adapted to be inserted between said spreading surfaces.
2. An instrument according to claim 1, wherein said displaceable wedge includes a displaceable slide and said instrument further comprises a bias means for biasing said displaceable slide.
3. An instrument according to claim 2, wherein said levers are interconnected at a pivot point and further comprising:
   a ring grip disposed at a first end of each of said pair of levers; and
   a pressure key means for activating said disengaging means, said pressure key means being located proximate the ring grip of one of said levers.
4. An instrument according to claim 1, wherein said locking means comprises:
   a pair of lugs one extending from each of said pair of levers, said pair of lugs each having locking teeth;
   wherein the locking teeth of said pair of lugs are mutually opposed and are selectively engaged by displacing said levers.
5. An instrument according to claim 4, wherein said spreading surfaces are formed on said lugs and adjacent said locking teeth and are adapted to be engaged by said wedge.
6. An instrument according to claim 2, wherein said slide has a pressure key and each of said levers has a ring grip at its one end, said key being located near the connecting portion of one of said levers and its ring grip.
7. An instrument according to claim 2, further comprising:
   a pressure key means for displacing said wedge in response to an applied force.
8. An instrument according to claim 2, further comprising:
   a stop pin means for limiting a maximum displacement of said displaceable slide in the direction of the spring bias.
9. In an instrument having a pair of pivotable levers operable to be locked in a first position by mutually engaged locking members disposed on projecting members having complimentary inclined surfaces, disengaging means comprising:
   a wedge means aligned with the inclined surfaces and adapted to be displaced to a position between the inclined surfaces;
   a pressure key connected to said wedge means and responsive to an applied force for displacing said wedge means between the inclined surfaces, whereby the engaged locking members are disengaged.
10. The instrument according to claim 9, further comprising:
    a biasing means for normally biasing said wedge means away from the inclined complimentary surfaces.

* * * * *